United States Patent [19]

Gough et al.

[11] Patent Number: 5,580,550
[45] Date of Patent: *Dec. 3, 1996

[54] COSMETIC COMPOSITION COMPRISING PARTICLES OF POLYISOBUTYLENE RESIN AND PROCESS FOR THE PREPARATION OF SAME

[75] Inventors: Anthony D. Gough, Merseyside; Joanne M. De Groot, Wirral; Jeffrey Price, Merseyside, all of United Kingdom

[73] Assignee: Chesebrough-Pond's USA Co., Division of Conopco, Inc., Greenwich, Conn.

[ * ] Notice: The term of this patent shall not extend beyond the expiration date of Pat. No. 5,441,730.

[21] Appl. No.: 430,003

[22] Filed: Apr. 27, 1995

Related U.S. Application Data

[62] Division of Ser. No. 49,095, Apr. 16, 1993, Pat. No. 5,441,730.

[30] Foreign Application Priority Data

Apr. 22, 1992 [GB] Great Britain .......................... 9208653

[51] Int. Cl.$^6$ .............................. A61K 7/06; A61K 7/075
[52] U.S. Cl. ....................................................... 424/70.11
[58] Field of Search ........................................... 424/70.11

[56] References Cited

U.S. PATENT DOCUMENTS 5,441,730  8/1995  Gough et al. .......................... 424/70.11

*Primary Examiner*—Peter F. Kulkosky
*Attorney, Agent, or Firm*—Milton L. Honig

[57] ABSTRACT

Cosmetic compositions comprising an emulsion, preferably an aqueous emulsion, including at least one cosmetic resin material, e.g. a hydrocarbon resin such as polyisobutylene, are made by direct emulsification of the resin without a solvent or carrier therefor. The direct emulsification may be achieved by a special mixing regime, with particular emulsifiers. The absence of solvent or carrier for the resin material avoids product thinning and gives several manufacturing and processing advantages.

9 Claims, 1 Drawing Sheet

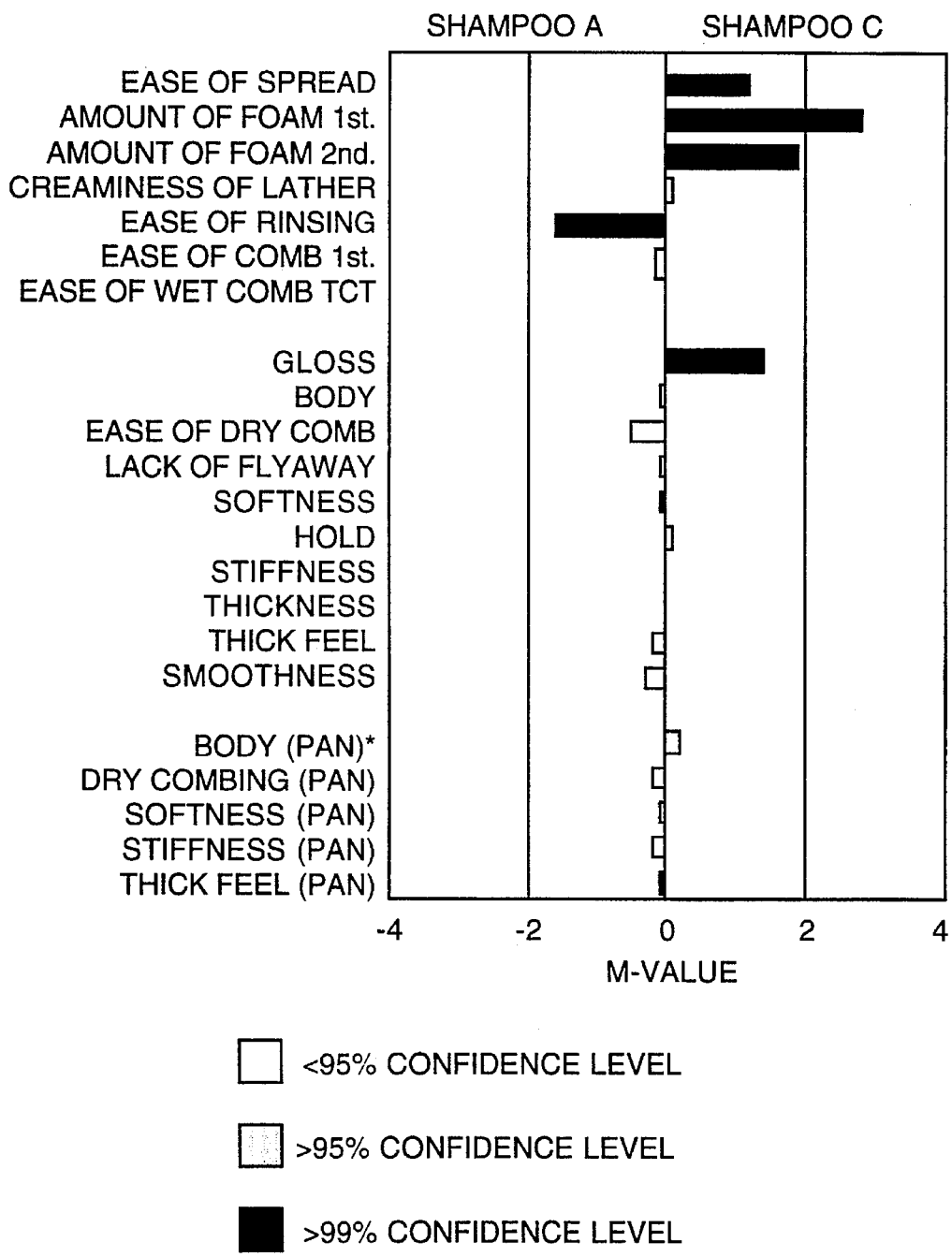

COSMETIC COMPOSITION COMPRISING PARTICLES OF POLYISOBUTYLENE RESIN AND PROCESS FOR THE PREPARATION OF SAME

This is a divisional application of Ser. No. 08/049,095 filed Apr. 16, 1993 now U.S. Pat. No. 5,441,730.

FIELD OF THE INVENTION

This invention relates to cosmetic compositions, more particularly to emulsion-based compositions containing one or more adhesive, resinous or resin-like materials for imparting one or more cosmetic benefits, e.g. to skin or hair. Especially, but not exclusively, the invention relates to cosmetic compositions for imparting stylabillity, enhanced body and/or a thicker feel to hair.

BACKGROUND OF THE INVENTION

The use of adhesive and/or resinous materials in cosmetic compositions is well known in the art, especially in the field of hair setting or styling aids and also skin-care products.

EP-A-240350 for example discloses the use of specific silicone polymers dissolved in a volatile carrier material for giving improved style retention to hair.

In FR-A-1102563 (published 1955) for instance there is disclosed an elastic cosmetic fixative for hair and moustaches, consisting of an elastomer dissolved in a hydrocarbon, especially Vaseline®.

A feature common to these known cosmetic products is the use of a solvent or carrier for the adhesive and/or resinous material. In some cases, especially skin care products, such a solvent or carrier is generally necessary in order to provide a product which is practically and aesthetically acceptable. In the field of hair care compositions, which are generally aqueous based, since the known adhesive and/or resinous materials are generally water-insoluble, a solvent or carrier has hitherto been necessary in order to successfully incorporate the material in the composition in a stable emulsified form.

The need to use such solvents or carriers brings with it several disadvantages. For example:

(a) products obtained through the use of such solvents or carriers are prone to significant thinning (i.e. low viscosity), thereby making it necessary to use a thickening ingredient to provide a product having a viscosity which is commercially and aesthetically acceptable;

(b) the need to use a solvent or carrier means that product manufacture requires at least one extra processing step which increases manufacturing time and cost;

(c) having to use a solvent or carrier means yet another formulation ingredient which increases the overall cost of raw materials;

(d) the known solvents or carriers, being generally volatile organic liquids, for safety reasons require strict handling and processing conditions, e.g. flame-proof equipment must be used. This contributes significantly to the overall cost and complexity of the manufacturing processes;

(e) volatile organic solvents or carriers generally act as foam suppressors and therefore impair the foamability and ease of spreading, e.g. on hair, of products, especially shampoos, containing them.

More recently, in our copending European patent application EP-A-0 498 119 there are disclosed hair styling compositions for imparting body and/or stylability to hair comprising, in addition to at least one of surfactant, conditioning agent and water or other volatile solvent, a per-alk(en)yl hydrocarbon material, e.g. polyisobutylene. The particularly preferred per-alk(en)yl hydrocarbon-containing compositions, and those actually exemplified therein, utilise an aforementioned solvent or carrier, e.g. a low molecular weight hydrocarbon, to dissolve or disperse the per-alk(en)yl hydrocarbon hair styling agent which preferably has a relatively high molecular weight. Therefore, even this latest proposal faces the above mentioned problems characteristic of the prior art cosmetic compositions containing adhesive and/or resinous materials.

SUMMARY OF THE INVENTION

We have now surprisingly found that, contrary to the general prior art teaching, it is not always necessary to resort to a solvent or carrier when incorporating adhesive and/or resinous cosmetic materials into emulsion-based cosmetic compositions, and techniques have now been found by which cosmetic resin materials can be incorporated by direct emulsification without the need for a conventional solvent or carrier. It is therefore now possible to ameliorate at least some of the above mentioned disadvantages associated with known cosmetic compositions containing adhesive and/or resinous materials.

Accordingly, in a first aspect the present invention provides a cosmetic composition comprising an emulsion including at least one cosmetic resin material, the cosmetic resin material being present as particles thereof emulsified directly without a solvent or carrier therefor.

In another aspect, the present invention provides a process for making a cosmetic composition including an emulsion comprising at least one cosmetic resin material, which process comprises the step of emulsifying particles of the cosmetic resin material directly without a solvent or carrier therefor.

In practical embodiments of the various aspects of the invention particular mixing regimes and emulsifiers are used to effect the direct emulsification of the cosmetic resin material.

BRIEF DESCRIPTION OF THE DRAWING

The present invention will be better understood from the following description in conjunction with the accompanying FIG. 1 which is the sole figure illustrating the results of hairdresser assessed half-head Salon Test of Shampoo A versus Shampoo C.

DETAILED DESCRIPTION OF THE INVENTION AND PREFERRED EMBODIMENTS

The Cosmetic Resin Material

As used in relation to this invention, "cosmetic resin" is not to be construed as being limited to any particular range of materials which are conventionally defined as "resins" because of their particular physical properties or chemical derivation, but rather the term as used herein means any high viscosity material, either natural or synthetic, which may be used in cosmetic regimes to give one or more tactile and/or visual benefits, especially to hair or skin, and particularly to give enhanced body, thicker feel and/or stylability to hair. That includes those materials which are solid or semi-solid at room temperature, as well as those which are liquids with high or moderate viscosities. The term does not cover oils or other low viscosity materials, eg. silicone oils, which are known in the art for incorporation in cosmetic emulsions often without the need for a separate low viscosity solvent or carrier material by virtue of their own lower viscosities and thus less stringent formulation requirements.

The present invention is useful in its application to cosmetic resins for use on the hair and/or the skin, particularly those for use on the hair, and especially those which impart stylability, body and/or a thicker feel to hair.

Particularly preferred cosmetic resin materials are synthetic cosmetic resins, especially hydrocarbon resins.

One preferred class of synthetic hydrocarbon resins for use in the invention are per-alk(en)yl hydrocarbons.

For these purposes a per-alk(en)yl hydrocarbon material is a branched alk(en)yl material, of which the side-groups are —H, $C_{1-4}$ alk(en)yl groups or (—H or $C_{1-4}$ alk(en)yl) substituted saturated or unsaturated cyclic hydrocarbons, and wherein at least 10% by number of the side-groups are other than —H, more preferably from 25% to 75%, most preferably from 40% to 60%. Preferred alkyl side-groups are methyl groups.

Preferably the weight average molecular weight of the per-alk(en)yl hydrocarbon material is between 150 and 10,000,000, more preferably 160 to 1,000,000, even more preferably 170–500,000. A particularly preferred weight average molecular weight range is 2,000 to 500,000.

An especially preferred embodiment of the present invention relates to the use of per-alk(en)yl hydrocarbon materials having a relatively high molecular weight of 20,000 to 1,000,000, more preferably 20,000 to 500,000, most preferably 40,000 to 200,000; these materials are especially effective in imparting body to hair.

In another embodiment of the invention the per-alk(en)yl hydrocarbon material used has a relatively low molecular weight of 2,000 to 20,000, more preferably 5,000 to 10,000. Such low molecular weight per-alk(en)yl hydrocarbon materials are available for example from Nippon Oil and Fats under the trade name POLYSYNLANE.

Preferred per-alk(en)yl hydrocarbon materials are polymers of butene, isoprene, terpene and styrene, and copolymers of any combination of these monomers, such as butyl rubber (poly isobutylene-co-isoprene), natural rubber (cis-1,4-polyisoprene) and hydrocarbon resins such as mentioned in the Encyclopedia of Chemical Technology by Kirk & Othmer (3rd edition vol 8, pp 852–869), for example aliphatic and aromatic petroleum resins, terpene resins etc.

Especially preferred are per-alk(en)yl hydrocarbon materials of the formula:

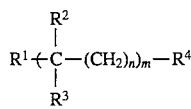

wherein:
n=0–3, preferably 1;
m=1–5000, preferably 2–2500;
$R^1$ is —H or a $C_{1-4}$ alkyl group; preferably methyl;
$R^2$ is a $C_{1-4}$ alkyl group; preferably methyl;
$R^3$ is —H or a $C_{1-4}$ alkyl group; preferably —H or methyl

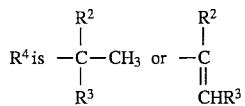

Especially preferred are polyisobutylene materials of the formula:

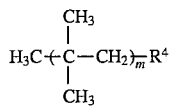

wherein m is 1–5000, preferably 2–2500, and $R^4$ is

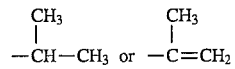

These materials are available for example from Presperse Inc. under the Permethyl trade name, and from Exxon under the Vistanex trade name.

In the cosmetic compositions of the invention the particle size of the emulsified cosmetic resin is not particularly critical and may depend at least to some extent on the conditions of the emulsification process. A typical average particle size is from about 0.01 to about 100μm, more typically from about 0.1 to about 10μm. By way of example, preferred cosmetic compositions according to the invention may have particle sizes of cosmetic resin material in the range 0.5 to 5μm, with about 90% of the particles being below 3μm in size and 50% of the particles being in the size range 1 to 2μm. Particle sizes may be measured for example using a Malvern Mastersizer instrument.

The total level of cosmetic resin material(s) in the cosmetic compositions of the invention is preferably from 0.01 to 20% by weight of the composition, more preferably from 0.1 to 10% by weight, even more preferably from 0.2 to 5% by weight, most preferably from 0. 5 to 2% by weight.

Other Ingredients

Cosmetic compositions in accordance with the present invention preferably contain one or more additional ingredients as may normally be found in products for use on the hair or the skin.

Thus cosmetic compositions according to the invention may take the form of hair treatment compositions or skin treatment compositions, depending upon the nature of the cosmetic resin material used and/or the additional ingredients employed. The invention is particularly useful for application to hair treatment products, but may also be used in application to skin products such as moisturising or cleansing compositions, creams, gels, suntan creams or lotions, and the like.

Preferred cosmetic compositions according to the invention are hair styling compositions, which may take the form of shampoos, conditioners, sprays, mousses or lotions. Particularly preferred hair styling compositions are shampoos and conditioners.

In addition to the advantages already mentioned above to be had using the direct emulsification technique of the invention, hair treatment compositions according to the invention have also been found to impart hair benefits which are at least as good as, and in some respects superior than, those obtainable with prior art formulations which rely on the use of volatile organic compounds as solvent or carrier for the cosmetic resin material. Attributes such as body, hold and stylability, for example, have been found to be comparable with those obtainable with the prior art systems, while visual benefits such as gloss have been found to be superior using the techniques in accordance with the invention.

Also characteristic of cosmetic compositions in accordance with the invention generally, are superior spreadability and foamability, particularly of hair and body shampoos.

Shampoo compositions (which may be in the form of body shampoos as well as in the form of hair shampoos) in accordance with the present invention comprise one or more surfactant materials for detergency purposes, preferably selected from anionic, nonionic, amphoteric and zwitterionic surfactants and mixtures thereof.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, akyl ether phosphates, alkyl ether carboxylates, and ∝-olefin sulphonates, especially their sodium, magnesium, ammonium and mono-, di- and tri-ethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of further suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants include condensation products of aliphatic ($C_8$-$C_{18}$) primary or secondary linear or branched-chain alcohols or phenols with alkylene oxides, usually ethylene oxide and generally 6–30 EO groups.

Other suitable nonionics include mono- or di-alkyl alkanolamides and alkyl polyglucosides. Examples include coco mono-or di-ethanolamide, coco mono-isopropanolamide, and coco di-glucoside.

Amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkyl amphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The total level of surfactant material(s), if present, in the cosmetic compositions of the invention is preferably at least 1% by weight of the composition, more preferably 2 to 40% by weight and most preferably from 5 to 30% by weight.

Hair styling compositions in accordance with the invention may comprise one or more hair conditioning agents.

Preferably, the amount of conditioning agent used is sufficient to impart overall hair conditioning properties to the composition when used on hair, so that such a composition provides hair conditioning and styling benefits simultaneously. However, a minor amount of conditioning agent may still advantageously be used, since although not being sufficient to render the composition a true conditioner, it is believed to ameliorate to some extent certain aspects of the bodying effect of the cosmetic resin material, such that the resulting overall styling and/or bodying and/or thicker feel effect of the composition is superior to that obtainable using the cosmetic resin material alone.

Suitable conditioning agents include cationic surfactants such as quaternary ammonium hydroxides, e.g. tetramethylammonium hydroxide, octyltrimethylammonium hydroxide, dodecyltrimethylammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof e. g. chlorides, cetylpyridinium hydroxide and salts thereof eg chloride, Quaternium-5, Quaternium-31, Quaternium-18, and mixtures thereof.

Alternative or additional conditioning agents include cationic polymers, volatile or non-volatile silicones, quaternized silicones (eg those materials available under the trade name ABILQUAT ex TH Goldschmidt), perfluoropolyethers (eg those materials available under the trade name FOMBLIN ex Montefluos), protein hydrolysates and quaternised protein hydrolysates.

Suitable cationic polymers include Guar hydroxypropyltrimonium chloride, Quaternium −19, −23, −40, −57, poly (dimethyldiallylammonium chloride), poly (dimethyl butenyl ammonium chloride)-, w- bis (triethanolammonium chloride), Poly (dipropyldiallylammonium chloride), Poly (methyl-beta propaniodiallylammonium chloride), Poly (diallylpiperidinium chloride), poly (vinyl pyridinium chloride), quaternised poly (vinyl alcohol), quaternised poly (dimethylaminoethylmethacrylate) and mixtures thereof.

Examples of suitable volatile silicone materials include those available commercially from Dow Corning as 244, 245, 344, 345 and 200 fluids (cyclopolymethylsiloxane blends), 200/5 fluid (a very short linear polydimethylsiloxane) and 1401 fluid (a mixture of polydimethylsiloxane gum and cyclopolymethylsiloxanes); from Union Carbide as TP503 fluid (an emulsion of polydimethylsiloxane gum in cyclopolymethylsiloxane) and Silicone 7202 and 7158; and from Stauffer Chemical as SWS-03314.

Suitable protein derivatives include lauryl dimonium hydroxy propylamino hydrolysed animal protein, available commercially under the tradename LAMEQUAT L, and hydrolysed keratin containing sulphur-bearing amino acids, available commercially under the tradename CROQUAT WKP.

Conditioning agents which are especially suitable include volatile or non-volatile silicone oils, such as for example polyalkylsiloxanes, polyalkylaryl siloxanes, silicone gums, cyclomethicones and aminofunctional silicones. Preferably these silicone materials are incorporated in the compositions as small particles, preferably of particle size 0.01 to 10 microns.

The preferred level of conditioning agent(s), if present, in compositions of the invention is up to 20%, for example from 0.01 to 10%, more preferably from 0.1 to 5% by weight.

Another ingredient that may advantageously be incorporated into the cosmetic compositions of the invention is a fatty alcohol material. The use of such a material is especially preferred in hair conditioning compositions which comprise one or more cationic surfactant materials. The combined use of fatty alcohol material and cationic surfactant is believed to be especially advantageous because this leads to the formation of a lamellar phase, wherein the cationic surfactant is dispersed.

Preferred fatty alcohols contain from 8 to 22 carbon atoms, more preferably 16 to 20. Examples of preferred fatty alcohols are cetyl alcohol and stearyl alcohol. The use of these materials is also advantageous in that they contribute to the overall conditioning properties of conditioning compositions of the invention.

The level of fatty alcohol material is conveniently from 0 to 10%, more preferably from 0.1 to 5% by weight of the composition. The weight ratio of cationic surfactant to fatty alcohol, if applicable, is preferably from 10:1 to 1:10, more preferably from 4:1 to 1:8, most preferably from 1:1 to 1:4.

A further optional ingredient of cosmetic compositions in accordance with the invention is a deposition aid for the cosmetic resin material. Any material capable of aiding the deposition thereof, especially onto hair or skin, may be used.

Conveniently the deposition aid is a cationic polymeric material. A preferred deposition polymer is a cationic derivative of guar gum, for example as available under the Jaguar trade name ex Meyhall.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR 162 which is a high transparency, medium viscosity guar having a low degree of substitution. Especially preferred is the use of Jaguar C13S.

The level of deposition aid, if used, is preferably from 0.001 to 10% by weight of the composition, more preferably 0.01 to 5% by weight, most preferably 0.05 to 2% by weight.

One or more other adjunct ingredients commonly found in cosmetic compositions may also be included in compositions of the present invention in minor amounts. Such additional ingredients include antibacterial agents, antidandruff agents such as zinc pyridinethione or Octopirox, foam boosters, pearlescers, opacifiers, suspending agents, preservatives, perfumes, dyes, colouring agents, viscosity modifiers, proteins, polymers, buffering agents, polyols and other moisturising agents, herb and other plant extracts, and sunscreen materials. The latter, by way of example, may be conveniently incorporated in the cosmetic compositions of the present invention by dissolving the sunscreen material in the cosmetic resin material which is then emulsified, in accordance with the teaching of our copending United Kingdom patent application No 9200764.0 filed Jan. 15, 1992, the disclosure of which is incorporated herein by reference.

The compositions of the invention are preferably based on an aqueous emulsion, typically with water forming at least one component of the continuous phase. The compositions, especially those which are hair care compositions, preferably comprise water in an amount of from about 20 to 99.5% by weight, more preferably 30 to 90% by weight, most preferably 40 to 70% by weight.

Other volatile solvents commonly used in known cosmetic products may be used instead of or in addition to water, for example lower alcohols, e.g. ethanol.

Process for Making the Cosmetic Compositions

In accordance with the second main aspect of the present invention, the cosmetic composition including an emulsion comprising at least one cosmetic resin material is made by a process which includes the step of emulsifying particles of the cosmetic resin material directly without a solvent or carrier therefor.

A preferred emulsification process which we have found to be effective for such direct emulsification comprises a mixing regime wherein the cosmetic resin material is emulsified by low shear rate (i.e. slow speed, for example with impeller tip speeds typically in the range 0.25 to 2.0 $ms^{-1}$), high shear stress mixing. The high shear stress aspect is mainly derived from the viscosity of the composition and the shape of the blades of the mixing apparatus, and the combination of these two mixing parameters enables the cosmetic resin to be emulsified as small particles directly into the base, preferably aqueous, composition.

A preferred mixing apparatus for carrying out the above technique is one commonly known as a "Z-blade" or "sigma-blade" mixer. Various examples of such mixers are commercially available, for example from Winkworth, Baker-Perkins, Sato Machinery, Gardner and Morton.

It is particularly preferred in accordance with the invention that one or more emulsifiers are included in the composition in the emulsification step, in order to assist the emulsification process and to stabilise the resulting emulsified resin particles.

Any emulsifier may be used which provides the necessary emulsion stability and examples of such emulsifiers are well known in the art and will therefore not be discussed at length here.

The emulsifier component may if desired or appropriate be provided by any surfactant present in the composition as a detergent material or may alternatively be constituted by another surfactant component present purely for its emulsifier properties.

A particularly preferred emulsifier is an anionic emulsifier, such as an alkylarylpolyalkoxyethylene sulphate, e.g. sodium alkylphenylpolyethoxyethylene sulphate, available commercially for example as Alipal CO-433.

The emulsifier may be used in any suitable amount, as appropriate to the processing conditions and materials used. By way of example, a suitable amount of emulsifier may be from about 0.1 to 10% by weight of the cosmetic resin material, or preferably from 1 to 5% by weight on the same basis.

In a preferred process according to this aspect of the invention, the cosmetic resin material is emulsified with the emulsifier into an aqueous continuous phase, to form a pre-emulsion. The pre-emulsion can then be added to any remaining ingredients of the final cosmetic composition by simple mixing and/or stirring.

If desired, one or more of the additional formulation ingredients, e. g. surfactant, or even a portion thereof may be incorporated in the pre-emulsification stage.

Embodiments of the present invention are further illustrated by the following examples.

EXAMPLE 1

Two shampoo compositions, A and B, comprising polyisobutylene as a hair styling resin were prepared by the following methods. Shampoo B was in accordance with the present invention; shampoo A was in accordance with the prior art.

SHAMPOO A

A pre-emulsion of polyisobutylene was made by mixing at room temperature the following ingredients in an Ystral high shear stirrer.

| Pre-emulsion ingredient | wt % |
|---|---|
| Vistanex LMMH[1] dissolved in Isopar L[2] | 60 |
| Sodium lauryl ether sulphate 2EO (22.5% aqueous solution) | 4 |
| Glycerol | 36 |

[1]Polyisobutylene, approx molecular weight 60,000, ex Exxon
[2]$C_{11-13}$ isoparaffin mixture, ex Exxon The pre-emulsion was then mixed, with stirring, with the remaining ingredients of the shampoo, to give a final composition as follows:

| Ingredient | wt % |
|---|---|
| Pre-emulsion | 1.5 |
| Sodium lauryl ether sulphate 2EO | 14 |
| Cocoamidopropylbetaine | 2 |
| Euperlan PK900[3] | 10 |
| Jaguar C13S | 0.1 |
| Formalin | 0.05 |
| BY 22-026[4] | 0.4 |
| NaCl | 5 |
| Perfume, colouring | qs |
| Water | to 100 |

[3]Mixture of triethylene glycol distearate and SLES 2EO, ex Henkel
[4]Polydimethylsiloxane, 50% aqueous emulsion, ex Toray Silicone

SHAMPOO B

A pre-emulsion of polyisobutylene was made by mixing at room temperature the following ingredients in a Winkworth twin-Z-blade mixer (model MZ150).

| Pre-emulsion ingredient | wt % |
|---|---|
| Vistanex LMMH | 58 |
| Alipal CO-433[5] | 1.4 |
| Water | 40.6 |

[5]Sodium alkyl phenyl polyethoxyethylene sulphate

The pre-emulsion was then mixed, with stirring, with the additional ingredients of the shampoo, to give a final composition as follows:

| Ingredient | wt % |
|---|---|
| Pre-emulsion | 1.6 |
| Sodium lauryl ether sulphate 2EO | 14 |
| Cocoamidopropylbetaine | 2 |
| Euperlan PK900 | 10 |
| Jaguar C13S | 0.1 |
| Formalin | 0.05 |
| BY 22-026 | 0.4 |
| NaCl | 5 |
| Perfume, colouring | qs |
| Water | to 100 |

Shampoo A was then tested against a placebo in a sensory test in vitro as follows:

Six 11.4 cm/4.5 g hair switches were prepared from Yugoslavian red tie hair ex Raoul. The switches were labelled numbers 1 to 6 and switches 1–3 were treated with shampoo A and switches 4–6 with a placebo shampoo identical to A except that the Vistanex LMMH/Isopor L pre-emulsion was absent.

All the switches were then set onto 30 mm diameter PTFE rollers and left to dry in a circulatory oven at 50° C. for 1 hour. The switches were then carefully removed from the rollers, allowed to cool at ambient temperature for 15 minutes and then tested for body by a trained panel of assessors using a paired comparison technique.

Twelve assessors were used and each panelist was presented with a total of six different permutations of pairs, each pair comprising a switch treated with Shampoo A and a switch treated with placebo shampoo.

Results of Test of Shampoo A Against Placebo

Out of the 72 paired comparisons the switch treated with Shampoo A was chosen 60 times. This is statistically significant at greater than 95% confidence level. Thus the switches treated with Shampoo A were perceived to have more body than those that were treated with the placebo shampoo.

Shampoo B was then tested against Shampoo A for body using the same procedure as above.

Results of Test of Shampoo B Against Shampoo A

Out of the 72 paired comparisons the switch treated with Shampoo B was chosen 34 times. Thus there was a statistically insignificant difference in body between the switches treated with shampoos A and B. Shampoo B was thus comparable to shampoo A at imparting the body attribute to hair.

EXAMPLE 2

A shampoo C was made by mixing the pre-emulsion of Shampoo B in Example 1 with additional shampoo ingredients to give a final formulation as follows:

| Ingredient | wt % |
|---|---|
| Pre-emulsion (as Shampoo B) | 1.5 |
| Sodium lauryl ether sulphate 2EO | 16 |
| Cocoamidopropylbetaine | 2 |
| Carbopol 980[6] | 0.4 |
| Jaguar C13S | 0.1 |
| Formalin | 0.1 |
| BY 22-026 | 0.4 |
| NaCl | 5.0 |
| Perfume, colour | qs |
| Water | to 100 |
| (pH adjusted to 5.5–8.0 with dilute NaOH if necessary) | |

[6]Thickener: Polymer of acrylic acid cross-linked with a polyfunctional agent, ex Goodrich Shampoo C was then tested against Shampoo A in a half-head salon test on thirty six panellists by trained hairdressers. Shampoo A was applied to half of the hair of each panellist, the hair being parted down the center, and Shampoo C was applied to the other half of each panellist's hair. Various in-use attributes and wet and dry hair properties were assessed for each half of the head. The hairdressers made one of three choices for each attribute assessed: left hand side better (score 1), no difference (score 0) and right hand side better (score −1). The results were analysed statistically and the M values, the sign and magnitude of which indicate which shampoo is superior for imparting a particular attribute, were plotted against the attributes.

M is defined as $$M = \ln\{P(C)/[1-P(C)]\}$$

where P(C) is an estimate of the probability that Shampoo C is preferred to Shampoo A.

The results are shown in the accompanying Figure 1.

It can be seen from FIG. 1 that Shampoo C was superior to Shampoo A for the attributes ease of spread and amount of foam on the first and second washes. Surprisingly, also Shampoo C was superior to Shampoo A on the gloss attribute. Whilst not intending to be bound by theory, the reason for this latter observation is thought to be due to the nature of the deposition of the polyisobutylene onto the hair being different for each shampoo such that the light scattering by the deposited material on the hair is less with Shampoo C than with Shampoo A.

It can also be seen that for the rest of the attributes including body and hold (style retention ) there was no significant difference between the shampoos. Thus the abilities of the shampoos to impart these attributes are comparable.

EXAMPLE 3

A skin moisturising cream in accordance with the invention was prepared by first making a pre-emulsion of polyisobutylene as for Shampoo B in Example 1 above.

The pre-emulsion was then mixed, with stirring, with the remaining ingredients of the skin cream to give a final product having the following composition:

| Ingredient | Wt % |
| --- | --- |
| Pre-emulsion (as for Shampoo B, Example 1) | 7.0 |
| Propyl paraben | 0.1 |
| Steareth-2[7] | 2.9 |
| Steareth-21[8] | 2.1 |
| Propylene glycol | 7.0 |
| Carbopol 934[9] | 0.3 |
| Methyl paraben | 0.2 |
| NaOH (10% aqueous) | 0.3 |
| Water | to 100 |

[7]CTFA designation for polyethylene glycol ether of stearyl alcohol (average PEG number of 2)
[8]CTFA designation for polyethylene glycol ether of stearyl alcohol (average PEG number of 21)
[9]Thickener: Polymer of acrylic acid cross-linked with a polyfunctional agent, ex Goodrich

We claim:

1. A process for preparing a shampoo composition comprising particles of polyisobutylene resin, the process comprising the steps of:
   (i) emulsifying particles of the resin material in a medium containing little or no organic solvent by low shear rate, high shear stress mixing to form emulsified particles;
   (ii) adding the emulsified particles to a shampoo base, comprising from 1 to 40% by weight of surfactant in water, thereby forming the shampoo composition in which the resin is present from 0.01 to 20 percent by weight as insoluble particles.

2. A process according to claim 1, wherein the emulsifying step is performed using a Z-blade or sigma-blade mixer.

3. A process according to claim 1, wherein the particles of resin are emulsified in a continuous phase of the medium comprising water.

4. A process according to claim 1, wherein the particles of resin are emulsified using at least one emulsifier.

5. A process according to claim 1, wherein the emulsifier is an anionic emulsifier.

6. A process according to claim 1, wherein the emulsifier is an alkylarylpolyalkoxyethylene sulphate.

7. A hair shampoo composition comprising:
   (i) a pre-emulsion having water as solvent consisting essentially of:
       a polyisobutylene resin present as the major other than water component of the pre-emulsion;
       an anionic emulsifier present in an effective amount to suspend the resin as insoluble particles, the pre-emulsion being present in the shampoo composition at a level to supply from 0.01 to 20% by weight of resin to the shampoo composition, the pre-emulsion containing little or no hydrophobic organic solvent and formed through emulsification by low shear rate and high shear stress mixing; and
   (ii) from 1 to 40% by weight of the shampoo composition of at least one surfactant.

8. A shampoo composition according to claim 7, wherein the emulsifier is present from about 0.1 to 10% by weight of the resin in the pre-emulsion.

9. A shampoo composition according to claim 7, wherein the emulsifier is an alkylarylpolyoxyethylene sulphate.

* * * * *